United States Patent [19]
Yamada et al.

[11] Patent Number: 5,488,043
[45] Date of Patent: Jan. 30, 1996

[54] METHOD FOR STABILIZING ACEPHATE AND A DRY PESTICIDAL FORMULATION CONTAINING THE STABILIZED ACEPHATE

[75] Inventors: Masahiro Yamada, Takarazuka; Yasuyuki Katayama, Toyonaka; Toshiro Ohtsubo, Sanda, all of Japan

[73] Assignee: Sumitomo Chemical Co., Ltd., Osaka, Japan

[21] Appl. No.: 360,042

[22] Filed: Dec. 20, 1994

[30] Foreign Application Priority Data

Dec. 20, 1993 [JP] Japan .................................. 5-319595
May 9, 1994 [JP] Japan .................................. 6-094813

[51] Int. Cl.$^6$ .................................................. A01N 57/28
[52] U.S. Cl. ............................. 514/120; 558/71; 558/178
[58] Field of Search .............................. 514/120; 558/71, 558/178

[56] References Cited

U.S. PATENT DOCUMENTS 5,352,674  10/1994  Cummings ............................... 514/120

FOREIGN PATENT DOCUMENTS 0304492  3/1989  European Pat. Off. .
5867603  10/1981  Japan .

*Primary Examiner*—Richard L. Raymond
*Attorney, Agent, or Firm*—Sughrue, Mion, Zinn, Macpeak & Seas

[57] ABSTRACT

The present invention relates to a method for stabilizing acephate which comprises adding a sodium salt of condensed phosphate and/or a synthetic silicic acid in which the surface silanol groups being alkylsilylated to acephate or acephate-containing dry pesticidal formulation and a stabilized acephate having added a sodium salt of condensed phosphate and/or a synthetic silicic acid in which the surface silanol groups being alkylsilylated.

13 Claims, No Drawings

METHOD FOR STABILIZING ACEPHATE AND A DRY PESTICIDAL FORMULATION CONTAINING THE STABILIZED ACEPHATE

The present invention relates to a method for stabilizing acephate and a dry pesticidal formulation containing the stabilized acephate.

Acephate (O, S-dimethyl acetylphosphoramidothioate) is a known compound having an insecticidal activity as described on page 1 of The Pesticide Manual 8th edition (published by The British Crop Protection Council, 1987) and used as an active ingredient for agricultural insecticide now, because of having effective controlling activities to various pests.

On the contrary to other organic phosphoric compounds having an insecticidal activity, acephate has a lower stability in a pesticidal formulation. Accordingly, acephate in the formulation is vigorously decomposed depending on the storage condition and the activity of acephate could not be often exhibited efficiently. Under the circumstances, there has been demanded a method for imparting a stability to acephate in the formulation and development of such a pesticidal composition which is capable of exhibiting the pesticidal activity of acephate efficiently.

The present inventors have conducted extensive study of such a subject matter. As a result, they have discovered that a sodium salt of condensed phosphate and/or a synthetic silicic acid in which the surface silanol groups being alkylsilylated may improve the stability of acephate in a dry formulation and the present invention has been completed.

Therefore, the present invention relates to a method for stabilizing acephate by adding an effective amount of a sodiums salt of condensed phosphate and/or an effective amount of a synthetic silicic acid in which the surface silanol groups being alkylsilylated, to the acephate, a method for stabilizing acephate in a dry formulation by mixing acephate with an effective amount of a sodium salt of condensed phosphate and/or an effective amount of a synthetic silicic acid in which the surface silanol groups being alkylsilylated and a dry pesticidal formulations containing acephate and an effective amount of a sodium salt of condensed phosphate and/or an effective amount of a synthetic silicic acid in which the surface silanol groups being alkylsilylated.

In the context of the present invention, the sodium salt of condensed phosphate refers to a compound in which two or more sodium phosphates are condensed via an oxygen atom, for example, sodium polyphosphate, sodium tripolyphosphate or sodium pyrophosphate.

The synthetic silicic acid in which the surface silanol groups being alkylsilylated used in the present invention may be usually prepared by alkylsilylating the surface silanol groups of a synthetic silicic acid produced by the wet process obtained by adding a mineral acid such as hydrochloric acid and sulfuric acid to an aqueous sodium silicate solution or of a synthetic silicic acid produced by the dry process obtained by decomposing silicon tetrachloride with an oxyhydrogen flame etc. with dialkyldichlorosilane or alkyltrichlorosilane. Said alkyl group is usually a lower alkyl group such as methyl and ethyl and the number of the surface silanol group is usually reduced substantially to 3 or less/nm$^2$. The synthetic silicic acid in which the surface silanol groups being alkylsilylated thus obtained is commercially available as Carplex® CS-701 mfg. by Shionogi Pharmaceuticals, Carplex® CS-801 mfg. by Shionogi Pharmaceuticals, Reolosil® MT-10 mfg. by Tokuyama Soda, Aerosil® R 972 mfg. by Degussa, Sipernat® D 17 mfg. by Degussa or Sipernat® D 10 mfg. by Degussa.

The amount of the sodium salt of condensed phosphate useful for stabilization of acephate is generally 0.01 to 10 parts by weight, preferably 0.05 to 1 part by weight to one part by weight of acephate.

The amount of the synthetic silicic acid in which the surface silanol groups being alkylsilylated which is useful for stabilization of acephate is generally 0.05 parts by weight or more, preferably 0.05 to 10 parts by weight to one part by weight of acephate.

The content of acephate in the dry pesticidal formulation of the present invention is generally 0.5 to 99% by weight, preferably 5 to 95% by weight. The content of the sodium salt of condensed phosphate in the dry pesticidal formulation is an amount in which acephate may be stabilized, usually 0.01 to 50% by weight, preferably 1 to 20% by weight, more preferably 1 to 10% by weight. The content of the synthetic silicic acid in which the surface silanol groups being alkylsilylated is an amount in which acephate may be stabilized, usually 1 to 99% by weight.

The dry pesticidal formulation using the sodium salt of condensed phosphate may usually contain a solid carrier for pesticidal formulation in addition to acephate and sodium salt of condensed phosphate. Said solid carriers include, for example, a mineral carrier such as kaolin clay, attapulgite clay, sericite clay, pyrophyllite clay, montmorillonite clay, zeolite, bentonite, acid clay, activated clay, serpentine, talc and diatomaceous earth, an inorganic salt such as sulfate, nitrate, chloride and carbonate, an inorganic carrier such as a synthetic carrier (e.g., silica), or an organic carrier such as sugars, starch, dextrin, flour, soy meal, corn meal and wood powder.

The dry pesticidal formulation of the present invention using the synthetic silicic acid in which the surface silanol groups being alkylsilylated may be ones consisting of acephate and the synthetic silicic acid in which the surface silanol groups being alkylsilylated, but additionally a solid carrier for the preparation may be contained therein. Said solid carriers include, for example, ones as mentioned above.

The solid carrier may be usually contained in 1 to 90% by weight, preferably 20 to 70% by weight in the dry pesticidal formulation.

The dry pesticidal formulation of the present invention may contain auxiliaries for pesticidal formulation, for example, at least one selected from the group consisting of surface active agent, coloring matter, perfume and known stabilizer, which are usually contained in 0.1 to 35% by weight, preferably 2 to 10% by weight.

The surface active agents that can be used in the present invention includes, for example, anionic surface active agents such as alkyl sulfates (e.g., sodium lauryl sulfate), alkylaryl sulfonates (e.g., sodium alkylnaphthalene sulfonate), lignin sulfonates (e.g., sodium lignin sulfonate), succinic acid ester derivative, polycarbonate, polyethyleneglycol alkylaryl ether sulfonate and a formaldehyde condensate of aromatic sulfonate, or nonioinic surface active agents such as polyoxyethylene alkylether, polyoxyethylene alkylarylether and polyoxyethylene arylarylether.

The dry pesticidal formulation of the present invention may additionally contain other pesticidal active ingredients, for example, pyrethroid compound such as Fenpropathrin, Fenvalerate and Esfenvalerate.

The dry pesticidal formulation of the present invention may be in the form of, for example, dust, driftless dust, wettable powder, water soluble powder, granule, water soluble granule, water dispersible granule, dry flowable, tablet or pellet, and these dry pesticidal formulations may be used by packaging those in a packaging container such as water soluble pack.

The dry pesticidal formulation of the present invention may be prepared according to a conventional method, for example, by admixing acephate and sodium salt of condensed phosphate and/or synthetic silicic acid in which the surface silanol groups being alkylsilylated, additionally a solid carrier and auxiliaries such as a surfactant if necessary in a mixer, pulverizing the mixture with a grinder such as air-mill, hammer mill, jet pulverizer and centrifugal pulverizer into, for example 20 μm or less of average particle size to obtain a powdery pesticidal formulation of the present invention, alternatively molding those pulverized mixture into granules using a compression press such as a roller compactor, extrusion granulator, pan granulator, fluidized bed granulator or rolling granulator to obtain a dry pesticidal formulation of the present invention.

The present invention will be explained with reference to the following formulation examples and test examples in detail, but the invention should not be construed as being limited to these examples only.

FORMULATION EXAMPLE 1

25 Parts by weight of acephate, 5 parts by weight of sodium tripolyphosphate, 4 parts by weight of sodium dodecylbenzenesulfonate, 2 parts by weight of sodium arylsulfonate formaldehyde condensate, 20 parts by weight of Tokusil® GU-N (synthetic silicic acid mfg. by Tokuyama Soda), and 44 parts by weight of kaolin clay were pulverized with a jet pulverizer and mixed in a mixer to obtain a wettable powder which is a dry pesticidal formulation of the present invention.

FORMULATION EXAMPLE 2

A wettable powder of the present dry pesticidal formulation was obtained according to Formulation Example 1, except that 10 parts of sodium tripolyphosphate were used instead of 5 parts of sodium tripolyphosphate and 39 parts of kaolin clay were used instead of 44 parts of kaolin clay.

FORMULATION EXAMPLE 3

25 Parts by weight of acephate, 20 parts by weight of Carplex® CS-701, 4 parts by weight of sodium dodecylbenzenesulfonate, 2 parts by weight of sodium arylsulfonate formaldehyde condensate and 49 parts by weight of kaolin clay were pulverized with a jet pulverizer and mixed in a mixer to obtain a wettable powder which is the present dry pesticidal formulation.

COMPARATIVE FORMULATION EXAMPLE 1

Comparative Formulation 1 was obtained according to Formulation Example 1, except that 5 parts by weight of kaolin clay were used instead of 5 parts by weight of sodium tripolyphosphate.

COMPARATIVE FORMULATION EXAMPLE 2

Comparative Formulation 2 was obtained according to Formulation Example 3, except that 20 parts by weight of Tokusil® GU-N (synthetic silicic acid mfg. by Tokuyama Soda) were used instead of 20 parts by weight of Carplex® CS-701.

TEST EXAMPLE

Each formulation obtained by said Formulation Examples and Comparative Formulation Examples was enclosed in an aluminum-laminated bag and stored in a temperature controlled container set at a specified temperature. The content of acephate before and after storage was determined with a gas chromatography, and the decomposition rate was calculated according to the following equation:

$$\text{Decomposition rate (\%)} = 100 - 100 \times \frac{\text{content of acephate after storage}}{\text{content of acephate before storage}}$$

Tables 1, 2 and 3 show the results.

TABLE 1

| Assayed Formulation | Decomposition rate (%) 40° C. | |
|---|---|---|
|  | after 1 month | after 3 months |
| Formulation Example 1 | 0 | 16 |
| Formulation Example 2 | 1 | 13 |
| Comparative Formulation Example 1 | 4 | 31 |

TABLE 2

| Assayed Formulation | Decomposition rate (%) 50° C. | |
|---|---|---|
|  | after 2 weeks | after 1 month |
| Formulation Example 1 | 3 | 26 |
| Formulation Example 2 | 2 | 20 |
| Comparative Formulation Example 1 | 15 | 44 |

TABLE 3

| Assayed Formulation | Decomposition rate (%) 50° C. | |
|---|---|---|
|  | after 2 weeks | after 1 month |
| Formulation Example 3 | 1 | 8 |
| Comparative Formulation Example 2 | 6 | 33 |

We claim:

1. A method for stabilizing acephate which comprises adding an effective amount of a sodium salt of condensed phosphate and/or an effective amount of a synthetic silicic acid in which the surface silanol groups being alkylsilylated, to acephate.

2. A method for stabilizing acephate in a dry formulation which comprises mixing acephate with an effective amount of a sodium salt of condensed phosphate.

3. A method according to claim 2 wherein the weight ratio of acephate to sodium salt of condensed phosphate is 1:0.01–1:10.

4. A method for stabilizing acephate in a dry formulation which comprises mixing acephate with an effective amount of a synthetic silicic acid in which the surface silanol groups being alkylsilylated.

5. A methyl according to claim 4 wherein the weight ratio of acephate to the synthetic silicic acid in which the surface silanol groups being alkylsilylated is 1:0.05–1:10.

6. A dry pesticidal formulation comprising acephate and an effective amount of a sodium salt of condensed phosphate and/or an effective amount of a synthetic silicic acid in which the surface silanol groups being alkylsilylated.

7. A dry pesticidal formulation comprising acephate and an effective amount of a sodium salt of condensed phosphate.

8. A dry pesticidal formulation comprising acephate and an effective amount of a synthetic silicic acid in which the surface silanol groups being alkylsilylated.

9. A dry pesticidal formulation according to claim 7 wherein the weight ratio of acephate to sodium salt of condensed phosphate is 1:0.01–1:10.

10. A dry pesticidal formulation according to claim 8 wherein the weight ratio of acephate to the synthetic silicic acid in which the surface silanol groups being alkylsilylated is 1:0.05–1:10.

11. A dry pesticidal formulation according to claim 7, wherein the formulation is dust, driftless dust, wettable powder, water soluble powder, granule, water soluble granule, water dispersible granule, dry flowable, tablet or pellet.

12. A dry pesticidal formulation according to claim 7, wherein the formulation is dust, driftless dust, water soluble powder, granule, water soluble granule, water dispersible granule, dry flowable, tablet or pellet.

13. A dry pesticidal formulation according to claim 8, wherein the formulation is dust, driftless dust, wettable powder, water soluble powder, granule, water soluble granule, water dispersible granule, dry flowable, tablet or pellet.

* * * * *